United States Patent [19]

Schamper et al.

[11] Patent Number: 4,722,835
[45] Date of Patent: Feb. 2, 1988

[54] DIBENZYL MONOSORBITOL ACETAL GEL ANTIPERSPIRANT STICK COMPOSITIONS

[75] Inventors: Thomas J. Schamper, Ramsey; Zsuzsanna M. Piso, North Haledon, both of N.J.

[73] Assignee: American Cyanamid Company, Stamford, Conn.

[21] Appl. No.: 880,649

[22] Filed: May 27, 1986

Related U.S. Application Data

[63] Continuation of Ser. No. 652,991, Sep. 21, 1984, abandoned.

[51] Int. Cl.$^4$ .......................... A61K 7/32; A61K 7/34; A61K 7/36; A61K 7/38
[52] U.S. Cl. ............................... 424/66; 424/DIG. 5; 424/67; 424/68
[58] Field of Search ........................ 424/65, 66, 68, 67, 424/DIG. 5

[56] References Cited

U.S. PATENT DOCUMENTS 4,346,079  8/1982  Roehl .................................... 424/65

OTHER PUBLICATIONS

Abstract of Japanese Patent No. 09882, 2/28/78.

Primary Examiner—Dale R. Ore
Attorney, Agent, or Firm—C. J. Fickey

[57] ABSTRACT

A method for producing solid gel antiperspirant sticks at a lower processing temperature, said sticks containing an acidic antiperspirant metal active compound, dibenzyl monosorbitol acetal as the gelling agent and at least one alcohol, a solvent which is an organic compatible, small organic compound of not greater than about five carbon atoms and is a good hydrogen bond donor or acceptor, and a stabilizing compound which is a basic metallic salt, and the gelled antiperspirant sticks formed by the process.

5 Claims, No Drawings

DIBENZYL MONOSORBITOL ACETAL GEL ANTIPERSPIRANT STICK COMPOSITIONS

This application is a continuation of application Ser. No. 652,991, filed Sept. 21, 1984, now abandoned.

The present invention relates to gelled cosmetic sticks in general. More particularly, it relates to gelled antiperspirant sticks containing an acidic antiperspirant-active compound. Still more particularly, it relates to antiperspirant sticks containing an acidic antiperspirant-active compound in the presence of dibenzyl monosorbitol acetal (DBMSA), a suitable organic solubilizing agent therefor, and a stabilizing agent, and to a method for producing said sticks at lower temperatures.

Many known cosmetic sticks consist largely of gelled alcoholic solutions. Sticks which exhibit a desirable transparent or translucent appearance are readily prepared using sodium stearate as the geeling agent: however, they cannot be prepared in the presence of acidic antiperspirant-active salts because the alkaline gelling agent will react with the salt. Opaque sticks are readily prepared from acidic antiperspirant salts using certain low melting waxy materials, such as stearyl alcohol. Translucent gel sticks with dibenzyl monosorbitol acetal have been made containing acidic antiperspirant-active salts but with high temperature processing. The sticks are stable, but there is a need for an easy, low temperature method of making acid-stable, translucent antiperspirant sticks.

Antiperspirant sticks containing dibenzyl monosorbitol acetal and acidic antiperspirant-active salts are disclosed by Roehl, U.S. Pat. No. 4,151,816 (Naarden). These sticks contain, in addition to the salt and gelling agent, a lower monohydric alcohol, such as ethanol; a di- or trihydric alcohol, such as 1,2-propylene glycol or 1,3-butylene glycol, and/or a lower polyglycol; a propylene/ethylene glycol polycondensate, having the formula:

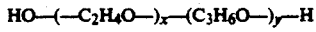

where $x/(x+y)$ lies between 0.6 and 1.0 and an average molecular weight of at least 500; and optionally, a mono- or dialkanolamide of a higher ($C_8$–$C_{20}$) fatty acid, such as N-(2-hydroxyethyl)cocamide.

In U.S. Pat. No. 4,346,079, Roehl discloses that a drawback to the sticks described above is their stickiness on application, which can be eliminated by entirely omitting, or greatly reducing, the polycondensate, and adding instead about 0.1 to 25 percent by weight of an oleaginous compound for stickiness control.

Applicants have found that the antiperspirant sticks described by Roehl must be made at elevated temperatures, e.g. at about 140° C. in order to solubilize the dibenzyl monosorbitol acetal with presently used solvents. The use of such elevated temperature is disadvantages for a number of reasons.

Forming the stick at such an elevated temperature accelerates the decomposition of the dibenzyl monosorbitol acetal. In addition, specialized equipment is required. Production equipment generally used in the manufacture of antiperspirant is designed to operate at a maximum of about 100° C. Moreover, the use of lower temperatures uses less energy, is safer, poses less vapor problems and will involve lower chemical reaction rates.

A further advantage of lower temperatures is better compatibility with fragrances, lower boiling components, and the plastic packaging into which the heated molten mixture is poured.

It is therefore an object of this invention to provide a composition and method whereby antiperspirant sticks containing dibenzyl monosorbitol acetal and an astringent metal compound may be manufactured at a lower temperature.

Another object is to define a solvent and stabilizer combination for dibenzyl monosorbitol acetal which is effective at lower temperatures.

These and other objects of my invention will become apparent as the description thereof proceeds.

In accordance with the present invention there are provided antiperspirant sticks containing dibenzyl monosorbitol acetal in the presence of acidic antiperspirant-active salts, said sticks comprising (a) about 1 to 50 percent of a solvent which is a small, polar organic compound; (b) about 0 to 80 percent by weight of a cosolvent (c) about 1 to 10 percent by weight of dibenzyl monosorbitol acetal; (d) about 0 to 35 percent by weight of an emollient; (e) about 5 to 25 percent by weight of an antiperspirant-active compound; (f) about 0 to 2.5 percent by weight of a $C_{12}$–$C_{20}$ fatty acid; and (g) 0.05 to 5 percent by weight of a gel stabilizer; said gel stabilizer being a basic metallic salt.

In commonly assigned, copending application Ser. No. 466,756, filed Feb. 15, 1983, now abandoned it was found that suitable primary solvents were organic compatible small compounds which are good hydrogen bond donors or acceptors. Some suitable compounds fitting within this class were cyclic esters, amides, amines, ketones, ureas, carbamates, sulfoxides and sulfones, and their open chain anologs. Specifically, compounds such as morpholine, pyridine, acetic acid, ethylene carbonate, propylene carbonate, N-methyl pyrrolidone, pyrrolidone, butyrolactone, dimethylsulfoxide, dimethyl formamide, 2-ethoxyethanol, caprolactam and the like, are included.

It has now been found that, although propylene carbonate and butyrolactone are excellent solvents, the gelled antipersirant stick is not sufficiently stabilized against deterioration, including high temperature degradation, by the stabilizing agents of the copending application.

The stabilizing agents of the present invention, suitable for stabilizing gelled sticks using propylene carbonate or butyrolactone as the primary solvent are basic metallic salts, e.g. zinc oxide, calcium acetate, magnesium oxide, calcium carbonate, calcium hydroxide, magnesium carbonate, sodium carbonate, zinc carbonate and potassium carbonate. Although the stabilizers of the present invention have been indicated as useful with propylene carbonate and butyrolactone, these stabilizers are also effective with additional solvents as disclosed in the above mentioned copending application.

In addition to the solvents set forth above, other solvents used in the invention are primary or secondary alcohols as follows: primary or low molecular weight alcohols such as ethanol, n-propanol, n-butanol, 2-methoxyethanol, 2-ethoxyethanol; ethylene glycol, 1,2-propylene glycol, diethylene glycol, and the like, and mixtures thereof. These solvents, because they are primary alcohols or because of their low molecular weight, tend to be more reactive towards dibenzyl monosorbitol acetal in the pressure of acidic antiperspirant-active salts. They are, however, excellent solvents for the preparation of the gelled sticks, particularly ethanol.

Alcohol with secondary alcohol groups or longer chain length, are less reactive towards dibenzyl monosorbitol acetal in the presence of acidic antiperspirant-active salts. These are also useful in the present invention. These solvents include isopropanol, isobutanol, diethylene glycol monomethylether, diethylene glycol monoethylether, 1,3-butylene glycol, 2,3-butylene glycol, dipropylene glycol, 2,4-dihydroxy-2-methylpentane, and the like, and mixtures thereof. A generally useful range for the primary and/or secondary alcohols is about 0 to 80 percent by weight of the stick composition. A preferred range is 35 to 65 percent.

The amount of stabilizers required will vary and will depend on the relative instability inherent in the solvents used, their relative proportions, and on the acidity of the antiperspirant-active salt used. Ordinarily the stabilizers will be used in an amount ranging from 0.02 to 5 percent by weight, preferably about 0.1 to 1 percent by weight, based on the total weight of the stick.

In addition to the solvent, dibenzyl monosorbitol acetal, antiperspirant-active salt and stabilizer, the sticks may contain other commonly used ingredients.

A liquid, volatile cyclic dimethylsiloxane may be added to the compositions to provide a desirable dry feel and emolliency. Other commonly used emollients, such as PPG-3 myristyl ether, octyl isononanoate, and the like, may be incorporated into the stick either in place of or in addition to the dimethylsiloxane. Although optional, it is preferred to use about 3 to 30 percent by weight of one or a combination of emollients.

The antiperspirant-active metal salts used in the present invention are the usual aluminum and/or zirconium compounds, especially aluminum hydroxy chlorides. They may be added in the form of a complex to enhance solubility in alcohols, such as aluminum chlorhydrex or Al/Zr chlorhydrex. The metal salts are preferably used in an amount of 10 to 20 percent by weight.

When solutions of aluminum hydroxychlorides are heated there may be a tendency towards premature gelation. This may be suppressed by the addition of a small amount of a $C_{12}$–$C_{20}$ fatty acid, such as stearic acid, without adversely affecting the stability of the gel. The amount added is preferably 0.2 to 1 percent.

In addition to the ingredients described above, the antiperspirant sticks may contain other ingredients in minor amounts, such as a dye color or a fragrance.

The present process involves dissolving the antiperspirant active in one phase and the dibenzyl monosorbitol acetal gellant in another phase. The two phases are then combined and poured into a mold or into the final package. Typically, a first phase is formed containing the acidic metal salt and a low molecular weight alcohol, at a temperature not exceeding about 75° C., and the second phase is formed containing the dibenzyl monosorbitol, the second phase is formed containing the dibenzyl monosorbitol acetal, the propylene carbonate, pyrrolidone or butyrolactone solvent, and the basic metallic salt at a temperature not exceeding about 1300° C., the second phase is cooled to about 70° to 80° C. and thereafter combined with the first phase to form a mixture, and the mixture is allowed to cool to form the antiperspirant stick. The other components are added to either of the two phases depending on the compatibility of the component with the phases as would be evident to those skilled in the art. If desired, one could employ more phases by forming a separate solution of some of the components. These separate phases then could be added to either of the two main phases or all of the phases could be poured together at the end as for example with a multi-stream filling head or in an inline mixer.

The following specific Examples 1 to 18 will illustrate the invention. The examples are shown in tabulated form in Table I.

The formulations were prepared as follows:

Preparation of propylene carbonate formulas:

The aluminum chlorhydrex of Phase A is dissolved in the ethanol with mixing. When the solution is clear, the myristyl ether is added. All the components of Phase B are heated with mixing until the dibenzylidene sorbitol is dissolved (no hotter than 105° C.). Phase B is cooled to 75° C. and added to Phase A at room temperature. The resulting mixture is poured into molds or the final package.

Preparation of butyrolactone formulas:

The aluminum chlorhydrex of Phase A is dissolved in the ethanol with mixing and heating. When clear the other components of Phase A are added and the Phase maintained at 40° C. Phase B is treated as described for propylene carbonate with phase B at 75° C. added to Phase A at 40° C.

TABLE I

|  | 1 | 2 | 3 | 4 | 5 | 6 | 7 | 8 | 9 |
|---|---|---|---|---|---|---|---|---|---|
| Phase A |  |  |  |  |  |  |  |  |  |
| Anhydrous ethanol | 42 | 41 | 41 | 41 | 41 | 41.5 | 41 | 41 | 41 |
| Aluminum chlorhydrex | 15 | 15 | 15 | 15 | 15 | 15 | 15 | 15 | 15 |
| PPG-3 myristyl ether | 15 | 15 | 15 | 15 | 15 | 15 | 15 | 15 | 15 |
| Acetamide MEA |  |  |  |  |  |  |  |  |  |
| Phase B |  |  |  |  |  |  |  |  |  |
| Propylene carbonate | 20 | 20 | 20 | 20 | 20 | 20 | 20 | 20 | 20 |
| Acetamide MEA | 5 | 5 | 5 | 5 | 5 | 5 | 5 | 5 | 5 |
| Dibenzyl monosorbitol acetal | 3 | 3 | 3 | 3 | 3 | 3 | 3 | 3 | 3 |
| Zinc acetate |  | 1 |  |  |  |  |  |  |  |
| Zinc stearate |  |  | 1 |  |  |  |  |  |  |
| Aluminum oxide |  |  |  | 1 |  |  |  |  |  |
| Calcium acetate |  |  |  |  | 1 |  |  |  |  |
| Zinc oxide |  |  |  |  |  | 0.5 | 1 |  |  |
| Magnesium oxide |  |  |  |  |  |  |  | 1 |  |
| Calcium carbonate |  |  |  |  |  |  |  |  | 1 |
| Calcium hydroxide |  |  |  |  |  |  |  |  |  |
| Sodium carbonate |  |  |  |  |  |  |  |  |  |
| Magnesium carbonate |  |  |  |  |  |  |  |  |  |
| Zinc carbonate |  |  |  |  |  |  |  |  |  |
| Butyrolactone |  |  |  |  |  |  |  |  |  |
| Calcium oxide |  |  |  |  |  |  |  |  |  |

TABLE I-continued

| Conditions at 60° C. | Liquid at 1 day | Very soft opaque gel at 10 days | Clear liquid at 1 day | Liquid at 1 day | Soft very hazy gel at 23 days | Soft opaque gel at 59 days | Soft opaque gel at 59 days | Very Soft, very hazy gel at 14 days | Slightly soft, opaque gel at 53 days |
|---|---|---|---|---|---|---|---|---|---|
| | 10 | 11 | 12 | 13 | 14 | 15 | 16 | 17 | 18 |
| Phase A | | | | | | | | | |
| Anhydrous ethanol | 41 | 41 | 41 | 41 | 43 | 47 | 47 | 47 | 41 |
| Aluminum chlorohydrex | 15 | 15 | 15 | 15 | 15 | 15 | 15 | 15 | 15 |
| PPG-3 myristyl ether | 15 | 15 | 15 | 15 | 15 | 15 | 15 | 15 | 15 |
| Acetamide MEA | | | | | 5 | 5 | 5 | 5 | |
| Phase B | | | | | | | | | |
| Propylene carbonate | 20 | 20 | 20 | 20 | | | | | 20 |
| Acetamide MEA | 5 | 5 | 5 | 5 | | | | | 5 |
| Dibenzyl monosorbitol acetal | 3 | 3 | 3 | 3 | 3 | 3 | 3 | 3 | 3 |
| Zinc acetate | | | | | | | | 1 | |
| Zinc stearate | | | | | | | | | |
| Aluminum oxide | | | | | | | | | |
| Calcium acetate | | | | | | | | | |
| Zinc oxide | | | | | | | | | |
| Magnesium oxide | | | | | | | | | |
| Calcium carbonate | | | | | | | | | |
| Calcium hydroxide | 1 | | | | | | | | |
| Sodium carbonate | | 1 | | | | | | | |
| Magnesium carbonate | | | 1 | | | | | | |
| Zinc carbonate | | | | 1 | | | | | |
| Butyrolactone | | | | | 14 | 14 | 14 | 14 | |
| Calcium oxide | | | | | | | | | 1 |
| Conditions at 60° C. | Very soft opaque gel at 14 days | Hard opaque gel at 52 days | Hard opaque gel at 52 days | Hard opaque gel at 29 days | Liquid at 1 day | Slightly soft opaque gel at 15 days | Very soft opaque gel at 5 days | Hazy liquid at 4 days | Soft opaque gel at |

Note: Samples are removed from study if very soft or liquid.

The gelled sticks were submitted to an accellerated storage stability test to determine their comparative stability. The test consisted of storing the sticks at a temperature of 60° C. (140° F.) and observing their condition periodically. The condition and storage time is shown at the bottom of Table I for each Example. One day storage at 60° C. is equivalent to two weeks at 45° C. which is the industry recognized high temperature stability for cosmetics.

Specific Examples 19 to 27 are illustrated in Table II together with the results of accellerated storage stability testing at 45° C. and 60° C.

Examples 19 to 21 were prepared according to the low temperature process of the present invention. Examples 22 to 27 were prepared according to the higher temperature process of copending, commonly assigned application Ser. No. 348,578, filed Feb. 12, 1982, now abandoned and refiled as Ser. No. 373,590, Apr. 30, 1982, now abandoned and refiled as Ser. No. 596,074, Apr. 3, 1984 now abandoned. The Examples illustrate that a stable stick may be obtained by the present process.

TABLE II

| | 19 | 20 | 21 | 22 | 23 | 24 | 25 | 26 | 27 |
|---|---|---|---|---|---|---|---|---|---|
| Phase A | | | | | | | | | |
| Anhydrous ethanol | 56 | 55.5 | 55 | 46.5 | 46 | 46.5 | 46 | 47.3 | 42.3 |
| Aluminum chlorohydrex | 15 | 15 | 15 | 15 | 15 | 15 | 15 | 15 | 15 |
| PPG-3 Myristyl ether | 15 | 15 | 15 | — | — | — | — | — | — |
| Acetamide MEA | 5 | 5 | 5 | 5 | 5 | 5 | 5 | — | 5 |
| Steareth 100 | — | — | — | — | — | — | — | 1 | 1 |
| Cyclomethicone | — | — | — | — | — | — | — | 5 | 5 |
| Stearic acid | — | — | — | — | — | — | — | 0.5 | 0. |
| Hydroxypropyl cellulose | — | — | — | — | — | — | — | 0.2 | 0. |
| Phase B | | | | | | | | | |
| 2-pyrrolidone | 6 | 6 | 6 | — | — | — | — | — | — |
| Dibenzyl monosorbitol acetal | 3 | 3 | 3 | 3 | 3 | 3 | 3 | 3 | 3 |
| Zinc oxide | — | 0.5 | 1 | 0.5 | 1 | 0.5 | 1 | — | — |
| Triethylene glycol | — | — | — | 30 | 30 | — | — | — | — |
| 1,3-Butylene glycol | — | — | — | — | — | 30 | 30 | 25 | 25 |
| 2,4-Dihydroxy-2-methylpentane | — | — | — | — | — | — | — | 3 | 3 |
| | * | Hard gel after 10 weeks at 60° C. (Conclusion of study) | | Solid gel after 5 weeks at 60° C. (Conclusion of study.) | | | | ** | *** |

*Liquid at 1 week at 60° C.
**Liquid at 5–6 weeks at 45° C.
***Not completely liquid by 27 weeks at 45° C.

We claim:

1. A solid gelled antiperspirant composition comprising:
   (a) 1 to 50 percent by weight of a solvent which is a small, polar organic and organic compatible compound selected from the group consisting of morpholine, pyridine, acetic acid, ethylene carbonate, propylene carbonate, N-methyl pyrrolidone, pyrrolidone, butyrolactone, dimethylsulfoxide, dimethyl formamide, 2-ethoxyethanol, and caprolactam:
   (b) 0 to 80 percent by weight of a cosolvent alcohol selected from the group consisting of ethanol, N-propanol, N-butanol, 2-methoxyethanol, 2-ethoxyethanol; ethylene glycol, 1,2-propylene glycol, diethylene glycol, isopropanol, isobutanol, diethylene glycol monoethylether, 1,3-butylene glycol, 2,3-butylene glycol, dipropylene glycol, and 2,4-dihydroxy-2-methylpentane:
   (c) 1 to 10 percent by weight of dibenzyl monosorbitol acetal;
   (d) 5 to 25 percent by weight of an acidic antiperspirant-active metal salt;
   (e) 0 to 2.5 percent by weight of a $C_{12}$ to $C_{20}$ fatty acid;
   (f) 0.02 to 5 percent by weight of a gel stabilizer which is a basic metallic salt.

2. A composition according to claim 1 wherein the acidic antiperspirant active metal salt is aluminum chlorhydrex or aluminum/zirconium chlorhydrex.

3. A composition according to claim 1 wherein the basic metallic salt has a cation selected from the group consisting of potassium, sodium, calcium, magnesium and zinc and anion selected from the group consisting of oxide, hyroxide, acetate and carbonate.

4. A composition according to claim 3 wherein said basic salt is zinc oxide.

5. A solid gel antiperspirant composition comprising:
   (a) 1 to 50 percent by weight of a solvent which is a small, polar organic and organic compatible compound selected from the group consisting of morpholine, pyridine, acetic acid, ethylene, carbonate, propylene carbonate, N-methyl pyrrolidone, pyrrolidone, butyrolactone, dimethylsulfoxide, dimethyl formamide, and 2-ethoxyethanol caprolactam;
   (b) 35 to 65 percent by weight of a cosolvent alcohol selected from the group consisting of ethanol, N-propanol, N-butanol, 2-methoxyethanol, 2-ethoxyethanol; ethylene glycol, 1,2-propylene glycol, diethylene glycol, isopropanol, isobutanol, diethylene glycol monomethylether, diethylene glycol monoethylether, 1,3-butylene glycol, 2,3-butylene glycol, dipropylene glycol, and 2,4-dihydroxy-2-methylpentane;
   (c) 1 to 10 percent by weight of dibenzyl monosorbitol acetal;
   (d) 10 to 25 percent by weight of an acidic antiperspirant-active metal salt selected from the group consisting of aluminum chlorhydrex and aluminum zirconium chlorhydrex;
   (e) 0.2 to 1 percent by weight of stearic acid;
   (f) 0.1 to 1 percent by weight of zinc oxide as a gel stabilizer;
   (g) 3 to 30 percent by weight of a liquid, volatile cyclic dimethylsiloxane.

* * * * *